US012797101B2

(12) United States Patent
Nagtegaal

(10) Patent No.: US 12,797,101 B2
(45) Date of Patent: Nov. 17, 2026

(54) SURGICAL DEVICE AND LOCKING COMPONENT THEREFOR

(71) Applicant: GYRUS ACMI, INC., Westborough, MA (US)

(72) Inventor: Marno Nagtegaal, Cardiff (GB)

(73) Assignee: GYRUS ACMI, INC., Westborough, MA (US)

(*) Notice: Subject to any disclaimer, the term of this patent is extended or adjusted under 35 U.S.C. 154(b) by 1079 days.

(21) Appl. No.: 17/692,532

(22) Filed: Mar. 11, 2022

(65) Prior Publication Data

US 2022/0313298 A1 Oct. 6, 2022

(30) Foreign Application Priority Data

Apr. 6, 2021 (GB) ..................................... 2104888

(51) Int. Cl.
*A61B 17/295* (2006.01)
*A61B 18/14* (2006.01)
(Continued)

(52) U.S. Cl.
CPC ........ *A61B 17/295* (2013.01); *A61B 18/1445* (2013.01); *A61B 2017/2946* (2013.01);
(Continued)

(58) Field of Classification Search
CPC .............. A61B 17/295; A61B 18/1445; A61B 2017/2946; A61B 2018/00077;
(Continued)

(56) References Cited

U.S. PATENT DOCUMENTS

2011/0238067 A1 9/2011 Moses et al.
2013/0304114 A1 11/2013 Joseph
(Continued)

FOREIGN PATENT DOCUMENTS

GB 2546275 A 7/2017
GB 2582319 A 9/2020

OTHER PUBLICATIONS

Dec. 22, 2021 Search Report issued in British Patent Application No. 2104888.9.
(Continued)

*Primary Examiner* — Joseph A Stoklosa
*Assistant Examiner* — Lindsay Regan Lancaster
(74) *Attorney, Agent, or Firm* — Schwegman Lundberg & Woessner, P.A.

(57) ABSTRACT

A locking component for a surgical device is disclosed, which is configured to prevent deployment of a blade when a first jaw member and a second jaw member of the surgical device are disposed in an open position and to permit deployment of the blade when the first and second jaw members are disposed in a closed position. The locking component includes a latch member, configured to prevent deployment of the blade by a mechanical interaction therewith when the latch member is in a first position. The locking component also includes a compliant body, connected to and disposed around the latch member, configured to bias the latch member to its first position. A surgical device incorporating the locking component and a method of operating the same is also disclosed.

20 Claims, 5 Drawing Sheets

(51) Int. Cl.
*A61B 17/29* (2006.01)
*A61B 18/00* (2006.01)

(52) U.S. Cl.
CPC ............... *A61B 2018/00077* (2013.01); *A61B 2018/00404* (2013.01); *A61B 2018/00589* (2013.01); *A61B 2018/0063* (2013.01); *A61B 2018/1455* (2013.01)

(58) Field of Classification Search
CPC ........... A61B 2018/00404; A61B 2018/00589; A61B 2018/0063; A61B 2018/1455; A61B 18/14
See application file for complete search history.

(56) References Cited

U.S. PATENT DOCUMENTS

| | | | | |
|---|---|---|---|---|
| 2015/0167345 | A1* | 6/2015 | Sosnowski | E04H 15/48 403/4 |
| 2015/0331443 | A1* | 11/2015 | Lamser | A61B 18/1445 74/532 |
| 2019/0307473 | A1* | 10/2019 | Fiksen | A61B 17/285 |
| 2022/0338910 | A1* | 10/2022 | Kucklick | A61F 2/30756 |

OTHER PUBLICATIONS

Dec. 10, 2024 Examination Report issued in United Kingdom Patent Applciation No. 2104888.9.

* cited by examiner

SURGICAL DEVICE AND LOCKING COMPONENT THEREFOR

TECHNICAL FIELD

The present disclosure relates to a surgical device, and in particular to a surgical forceps device wherein a mechanical blade provides tissue cutting.

BACKGROUND OF THE DISCLOSURE

Surgical forceps are used to clamp tissue or vessels before cutting and/or sealing the tissue. In some arrangements, a surgical device includes means to clamp tissue, such as by the opening and closing of jaw members thereon. Electrosurgical devices may include jaw members that are connected to an electrosurgical energy source, enabling them to seal tissue or vessels held therebetween. Some arrangements include a blade which can be deployed between the jaw members to cut tissue. Typically, the blade should only be deployed when the tissue is properly clamped, in order to avoid cutting other tissues during surgery. Therefore, it is preferable for surgical devices to include a mechanism that prevents the blade being deployed when the jaw members are open, and permits the blade to be deployed when the jaw members are closed.

GB2546275A discloses a surgical instrument having an elongate shaft and a blade assembly. A trigger mechanism provides means for deploying and retracting the blade assembly.

GB2582319A discloses a pivot assembly for surgical forceps with a deployable blade, wherein the blade is prevented from deploying while jaws of the forceps are open, by a mechanical interaction with a pivot pin.

SUMMARY OF THE DISCLOSURE

Embodiments of the present disclosure provide an improved surgical instrument having opposing jaw members extending from a handle. The jaw members form part of an end-effector capable of several different operations, including grasping, cutting, sealing and/or coagulating tissue or vessels. The opening and closing of the jaw members is performed by manipulating the handle by a scissor action. A cutting blade can be deployed using a trigger to cut tissue clamped by the jaw members. The device includes a locking mechanism which prevents the cutting blade being deployed unless the jaw members are in a closed position. The locking mechanism includes a locking component formed from a compliant body that is compressed when the jaw members are closed. Fixed to the compliant body is a latch member which can mechanically interact with the blade. The locking component is configured such that when the jaw members are open, the latch mechanism prevents the blade from being deployed. The focus of the disclosure is on the shape and configuration of the locking component which must be capable of preventing the cutting blade from being deployed when the jaws are in an open position.

In view of the above, from one aspect the disclosure provides a locking component for a surgical device configured to prevent deployment of a blade when a first jaw member and a second jaw member of the surgical device are disposed in an open position and to permit deployment of the blade when the first and second jaw members are disposed in a closed position, the locking component comprising:

a latch member, configured to prevent deployment of the blade by a mechanical interaction therewith when the latch member is in a first position; and a compliant body, connected to and disposed around the latch member, configured to bias the latch member to its first position.

Such an arrangement improves on those known in the art by providing a single component capable of preventing the blade from being deployed when the jaws are open, without the need for any additional user input. This arrangement provides an advantage over prior devices that may include a sliding mechanism to lock and unlock the blade when the jaws are closed. Instead, the device disclosed herein automatically removes the obstacle to blade deployment when the jaws are closed. Compared to prior devices such as those that include open-ended cantilever swing mechanisms or coil spring mechanisms, which rely on being fixed to other components, the locking component provided herein does not need to be fixedly connected to other components of the surgical device. This has the advantage of reducing the number of components required to assemble a surgical device, which reduces costs and assembly time. Moreover, this arrangement is advantageous because it provides a more repeatable biasing force with a reduced risk of creep. By disposing the compliant body around the latch member, the locking component is more compact and self-contained. This further simplifies manufacture of the locking component and its assembly within a surgical device.

The compliant body may be configured to bias the latch member away from a second position, in which the latch member is disengaged from the blade. The first position of the latch member may correspond to the open position of the first and second jaw members, and the second position of the latch member may correspond to the closed position of the first and second jaw members.

The compliant body may be planar. Otherwise stated, the compliant body may lie parallel to a plane and may be flat. The compliant body may be configured to exert a biasing force in a direction parallel to the plane. Preferably, the compliant body is not a coil spring. This has the advantage of facilitating a simpler and more compact surgical device assembly.

The latch member may be a projection extending out of the plane of the compliant body. The latch member may be a pin or a cylindrical rod. The latch member may extend in a direction perpendicular to the compliant body. This has the advantage of providing a locking component wherein the compliant body can be compressed in a planar direction to move the latch member in a direction parallel to the plane of the compliant body, thereby allowing the compliant body to bias the latch member to its first position without requiring components to be pivotally or slideably connected to each other. This further simplifies manufacture and assembly.

The compliant body may comprise a loop of material. Preferably, the compliant body comprises a closed loop of compliant material. At least a portion of the loop may have a rectangular cross section. This provides a predictable and repeatable biasing force. The compliant body and the latch member may be an integral component. That is to say, the compliant body and the latch member may be comprised within a single component without requiring any additional manufacturing or assembly steps to connect them.

The locking component may comprise a polymer. The locking component may comprise a single moulding. In particular, the compliant body and the latch member may be comprised in the same, single moulding. This provides a locking component that can be manufactured quickly and reliably, wherein the relative positioning of the latch member within the compliant body is repeatable, thereby reducing the need for precise assembly steps. This may also facilitate the locking component to be produced by additive manufacturing such as 3D printing.

The compliant body may be stadium-shaped. Otherwise stated, the compliant body may be a discorectangle or obround. The compliant body may have two straight portions and two arc portions. The arc portions may be semicircular. The straight portions may extend tangentially from the ends of the arc portions. The straight portions may be parallel. The straight portions may be separated by a first distance, wherein an inner diameter of at least one arc portion is equal to the first distance. The mean separation between the straight portions may be equal to the mean inner diameter of the arc portions.

The locking component may further comprise a rib. The rib may be connected to the latch member and to the compliant body. The rib may comprise a substantially rectangular portion lying in the plane of the compliant body. The latch member may extend from the rib. The rib may be enclosed within the loop defined by the compliant body. The rib may be fixed to a straight portion of the compliant body. The rib may extend from the first straight portion in a direction towards the second straight portion.

The rib may have one or more straight edges extending in a direction lying in the plane of the compliant body. This provides an advantageous locking component wherein the latch member is integrally connected to the compliant body via the rib. This also provides an advantageous construction wherein one or more straight sides of the rib are provided to slideably engage a portion of the surgical device in order to constrain the movement of the latch member in the plane of the compliant body.

The locking component may comprise an arm. The arm may be connected to the same straight portion of the compliant body as the latch member. The arm may extend outside of the boundary of the compliant body, parallel to the plane thereof. The arm may be connected to the same point along the compliant body as the latch member. The arm may extend from the first straight portion in a direction away from the second straight portion. Advantageously, this provides a feature which can interact with a handle or lever of a surgical device to transfer the force of closing the jaws to the locking component, in order to move the latch member away from its first position.

The locking component may consist of a single moulding. The single moulding may be any suitable polymer. The single moulding may comprise any or all of: the compliant body, the latch member, the rib and the arm. Advantageously, this provides a complete solution in a single moulded component which does not need to be fixedly connected to any other components in order to function in a surgical device.

From another aspect of the present disclosure, there is provided a surgical device comprising the locking component described hereinabove.

The surgical device may comprise:

a hand-piece, first and second jaw members extending from the hand-piece, configured to be open and closed in response to manipulation of the hand-piece, a blade assembly comprising a blade and a trigger mechanism for deploying the blade towards the first and second jaw members, and a locking component as described hereinabove.

The latch member of the locking component may be a first latch member, configured to mechanically interact with a second latch member of the blade. The second latch member may be a slot or notch configured to receive the first latch member. A longitudinal axis of the blade may be parallel to the plane of the compliant body. A planar surface of the blade may be parallel to the plane of the compliant body. The compliant body and the blade may be arranged such that the second latch member lies within the boundary of the compliant body. In other words, the compliant body may form a loop around the second latch member.

The hand-piece may comprise a handle portion and a lever. The first and second jaw members may be configured to close together when the lever is forced towards the handle portion. The locking component may be comprised in the handle portion. The handle portion may comprise first and second sidewalls, between which the locking component may be located in the surgical device. An internal surface of one of the first and second sidewalls may comprise a rail, along which the rib of the locking component is configured to slide. The rail may extend in a direction perpendicular to a longitudinal axis of the blade. The handle portion may comprise an aperture out of which the arm of the locking component is configured to protrude towards the lever.

The blade assembly may comprise a trigger arm. The trigger arm may be pivotally connected to the blade by a pivot pin. The handle portion may comprise a support. The support may be fixed between the first and second sidewall of the handle portion. The support may comprise a track configured to receive the pivot pin in order to constrain the motion of the blade in a direction along its longitudinal axis. In this respect, a dimension of the track may correspond to a dimension of the pivot pin. The support may comprise a notch through which the first latch member may be configured to extend. A dimension of the notch may correspond to a dimension of the first latch member. The notch may extend in a direction perpendicular to the track to constrain the motion of the first latch member in a direction perpendicular to the longitudinal axis of the blade.

From another aspect of the disclosure, there is provided a surgical device comprising:

a hand-piece, first and second jaw members extending from the hand-piece, configured to be open and closed in response to manipulation of the hand-piece, a blade assembly comprising a blade and a trigger mechanism for deploying the blade towards the first and second jaw members, and a locking component, comprising a first latch member, the first latch member being configured to mechanically interact with a second latch member comprised in the blade when the first latch member is in a first position, in order to prevent deployment of the blade, wherein the locking component further comprises a compliant body, configured to bias the latch member to its first position.

The first latch member and the compliant body may be comprised in a single moulded component.

From another aspect of the disclosure, there is provided a method of operating a surgical device as described hereinabove.

The method may comprise the steps of:

providing a surgical device as described hereinabove, moving the lever towards the handle portion to close the first and second jaw members, wherein closing the first and second jaw members causes the latch member to move from a first position, in which the latch member prevents the blade from being deployed by a mechanical interaction therewith, and a second position, in which the latch member is disengaged from the blade to permit deployment thereof, activating the trigger mechanism to deploy the blade.

The method may further comprise releasing the lever such that the jaw members move to an open configuration. Releasing the lever preferably causes the latch member to return to its first position due to a biasing force provided by the compliant body.

From another aspect of the disclosure, there is provided a method of operating a surgical device having a hand-piece, opposing jaw members extending from the hand-piece, a blade and a locking component, the locking component comprising a compliant body, lying parallel to a first plane, and a latch member configured to mechanically interact with the blade to prevent the blade being deployed when the latch member is in a first position, the method comprising the steps of:

manipulating the hand-piece to close the opposing jaw members, wherein closing the jaw members exerts a force on the latch member parallel to the first plane, such that the latch member is moved away from the first position so as to disengage the blade, and activating a trigger mechanism to deploy the blade.

In some embodiments, the surgical instrument may be an electrosurgical instrument, and the jaw members are provided with electrically conductive plates that make contact with tissue held between the jaw member when in use. The electrically conductive plates can be electrically connected to an electrosurgical generator, to receive in use, at the command of the surgeon, a RF electrosurgical signal sufficient to cause coagulation or sealing of tissue held between the jaws. Provision of such electrosurgical elements permits a mode of operation where tissue to be cut, such as a blood vessel, can be grasped within the jaws and sealed by the application of the RF electrosurgical signal from the RF electrosurgical generator operating in coagulation mode to the electrically conductive plates. Once the blood vessel is sealed, the blade can then be deployed between the jaws, once the latch member is disengaged, in order to cut the sealed tissue.

BRIEF DESCRIPTION OF THE DRAWINGS

Further features and advantages of the present disclosure will become apparent from the following description of embodiments thereof, presented by way of example only, and by reference to the drawings, in which.

DETAILED DESCRIPTION

A surgical device and a locking device therefor is described herein in the context of an electrosurgical system for performing procedures such as clamping, cutting and sealing of tissues using an end effector. The system includes an electrosurgical generator capable of providing a radiofrequency (RF) output, which may be controlled by various user inputs such as push buttons and switches on the electrosurgical generator and/or surgical device itself. A hand-piece of the surgical device is connected to the generator by a connection cord capable of transmitting power and RF signals thereto. The hand-piece provides a means with which a practitioner may manipulate the end effector. The surgical device is not limited to use within an electrosurgical system but may also be employed in a device without any electrosurgical capabilities, such as those used for the clamping and cutting of vessels.

The present disclosure is particularly applicable to scissor-action devices, such as those comprising a pair of jaw members which can be used to grip tissue or vessels during surgery. The hand-piece can be manipulated by a user to open and close the jaws. In order to cut tissue, a blade is provided which can be deployed, by a trigger mechanism, through an opening between the jaw members. A locking component of the device prevents the blade from being deployed when the jaw members are open. The locking component includes a compliant body that can flex and deform but will return to its original shape when released. The compliant body is a closed loop of material and lies within a first plane. A latch member, for example a pin, is fixed to the compliant body and extends in a direction that is non-parallel to the plane of the compliant body. When the locking component is installed in a surgical device, the latch member engages a portion of the cutting blade to prevent the blade from being deployed. When the jaws are closed, a force is transferred to the latch member to move it in a direction parallel to the plane of the compliant body. This releases the latch member from the blade and allows the blade to be deployed. Once the jaws are opened again, the compliant body returns to its original position such that the latch member re-engages the blade and prevents deployment thereof.

Figure 1:
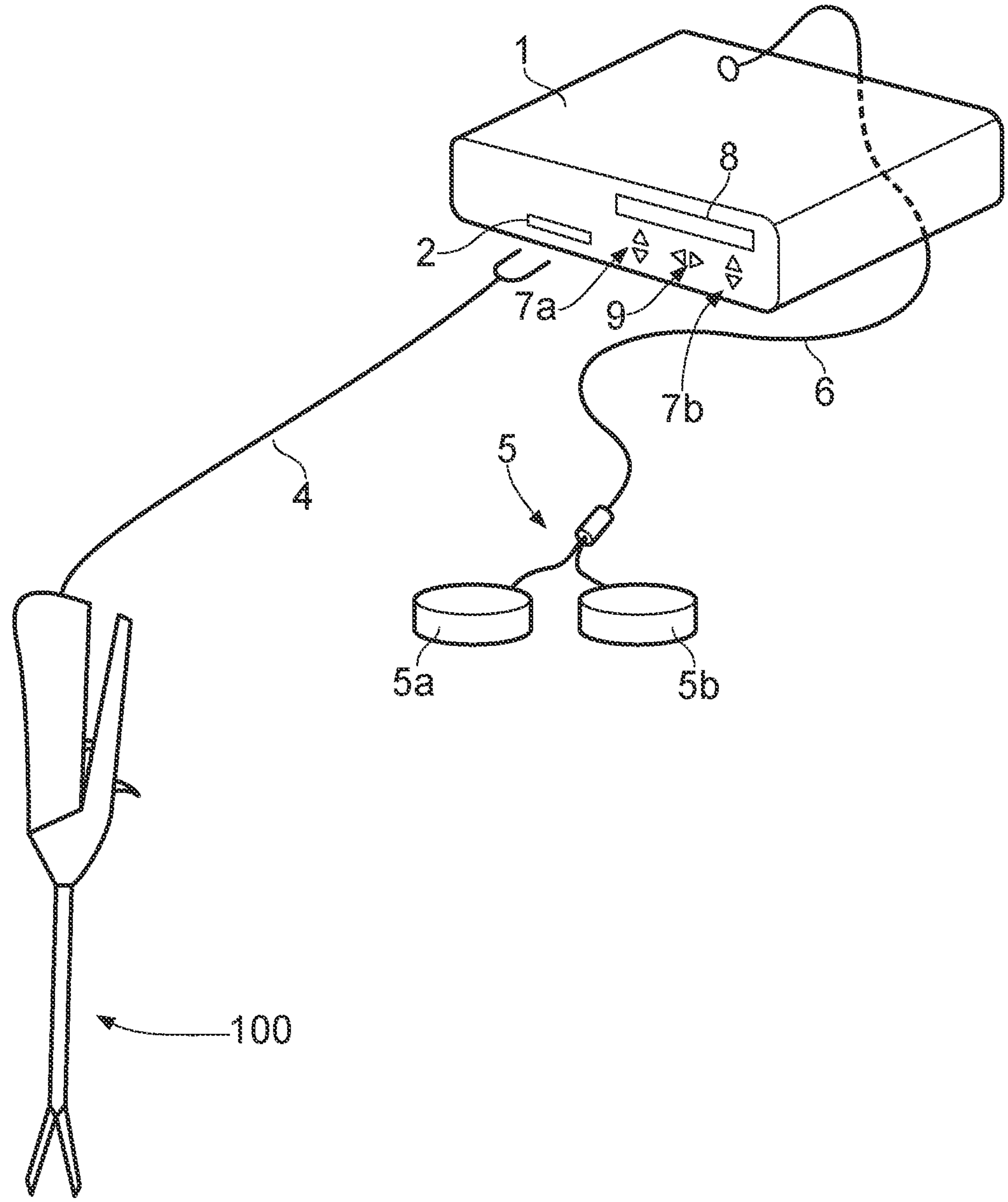
FIG. 1 is a schematic diagram of an electrosurgical system according to an embodiment.

Referring to the drawings, FIG. 1 shows electrosurgical apparatus including an electrosurgical generator 1 having an output socket 2 providing a radio frequency (RF) output, via a connection cord 4, for a surgical device 100. Activation of the generator 1 may be performed from the device 100 via a hand-switch (not shown) on the device 100, or by means of a footswitch unit 5 connected separately to the rear of the generator 1 by a footswitch connection cord 6. In the illustrated arrangement, the footswitch unit 5 has two footswitches 5*a* and 5*b* for selecting between different modes of the device 100. The generator front panel has push buttons 7*a*, 7*b* for respectively setting the power used for sealing vessels, which is indicated in a display 8. Push buttons 9 are provided as an alternative means for selection between the modes of operation.

Figure 2:
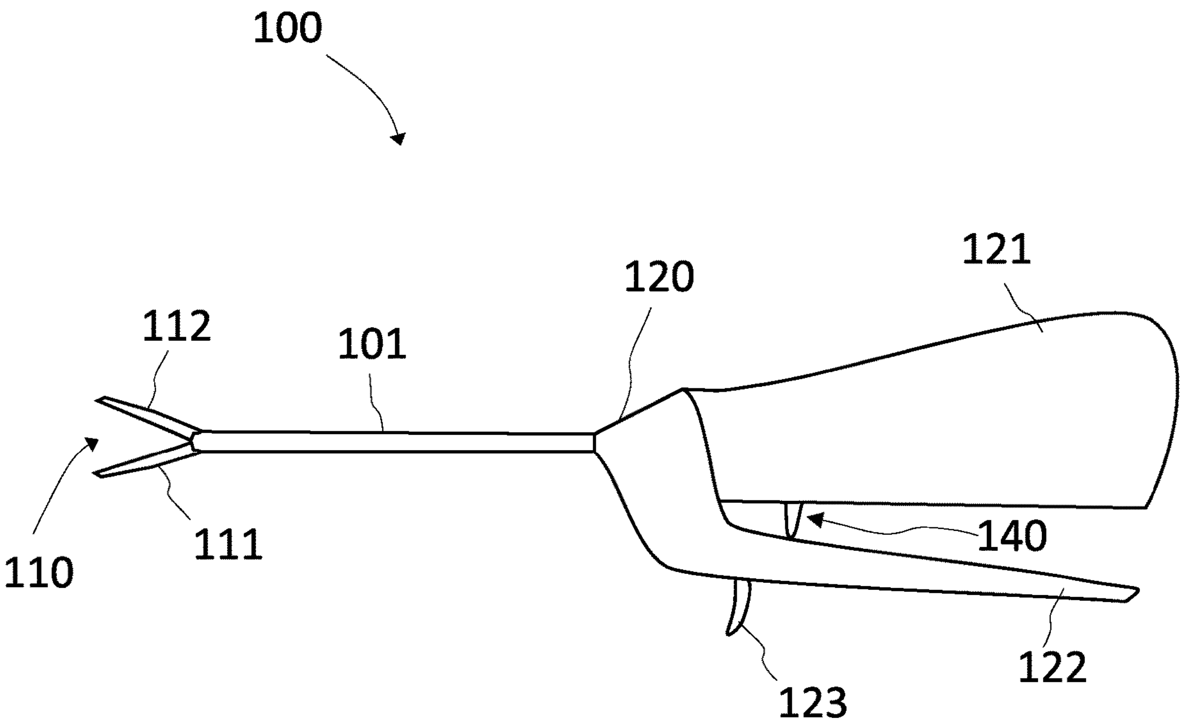
FIG. 2 is a side view of a surgical device according to an embodiment.

FIG. 2 shows the surgical device 100 that forms the basis of an embodiment of the present disclosure. The surgical device 100 comprises a hand-piece 120 and an elongate shaft 101. The elongate shaft 101 extends along a substantially longitudinal axis of the surgical device 100. The elongate shaft 101 is connected at a proximal end to the hand-piece 120 and is connected to an end effector 110 at a distal end. The hand-piece 120 comprises a handle portion 121 and a lever 122, shown in FIG. 2 in the open position. The lever 122 is pivotally connected to the handle portion 121 such that a user may move the hand-piece 120 to a closed position in which the lever 122 is moved towards the handle portion 121. The hand-piece 120 is biased towards the open position by a biasing means (not shown) and configured such that when a user releases the lever 121, it is returned to the open position away from the handle portion 121.

The surgical device 100 further comprises a blade (not shown in FIG. 1) for cutting tissue and vessels. The blade comprises a first end located within the handle portion 121 and extends along the elongate shaft 101 up to a second end located towards the end effector 110. Therefore, the blade has a longitudinal axis parallel to the longitudinal axis of the elongate shaft 101. The blade comprises a cutting portion (not shown) at the second end which has an edge suitable for cutting vessels and tissue. The surgical device further comprises a trigger mechanism (not shown) configured to deploy the blade such that the cutting portion at the second end extends beyond the elongate shaft 101 to protrude out of the end effector 110. Any conventional trigger mechanism that is able to deploy the blade with sufficient force to cut tissue may be employed. The trigger mechanism is activated by a trigger 123. In FIG. 2, the trigger is shown to extend from the lever 122, but the trigger 123 may be fixed to any part of the hand-piece 120 that permits operation when in use by a practitioner. The trigger mechanism may be configured such that pulling the trigger 123 deploys the blade and then immediately returns the blade to its resting position.

The end effector 101 comprises a first jaw member 111 and a second jaw member 112. The first and second jaw members 111, 112 are pivotally connected to the distal end of the elongate shaft 101. In an alternative arrangement, one of the jaw members 111, 112 is provided in fixed relation to the elongate shaft 101 while the other jaw member 111, 112 is pivotally connected to the elongate shaft 101. The jaw members 111, 112 comprise a pair of opposing surfaces configured to grip and clamp tissue or vessels. In certain arrangements, the jaw members comprise one or more electrodes arranged on or as the inner opposed surfaces of the jaws. In such arrangements, the electrodes are electrically connected to the handle 120 to receive an electrosurgical RF signal for the sealing or coagulation of tissue. The jaw members 111, 112 are further provided with a slot or other opening within the inner opposed surfaces through which the blade may protrude when deployed.

In an alternative embodiment (not shown), the surgical device does not comprise an elongate shaft. Instead, the end effector 110 can be directly connected to the hand-piece 120. The handle portion 121 may be fixedly connected to the first jaw member 111 to form a first scissor portion, while the lever 122 may be fixedly connected to the second jaw member 112 to form a second scissor portion. By crossing the first scissor portion with the second scissor portion and providing a pivot point therebetween, the action of the surgical device may be configured similarly to that of a typical pair of scissors or pliers.

Irrespective of the way in which the end effector 101 is connected to the hand-piece 120, the surgical device 100 is configured such that moving the two portions of the hand-piece together (for example by closing the lever 122 towards the handle portion 121), moves the jaw members 111, 112 towards each other, so that the end effector 110 can grip or clamp tissue or vessels. The surgical device 100 is configured such that only when the jaw members 111, 112 are closed may the blade be deployed. In this respect, the surgical device 100 comprises a locking component 140.

Figure 3A:
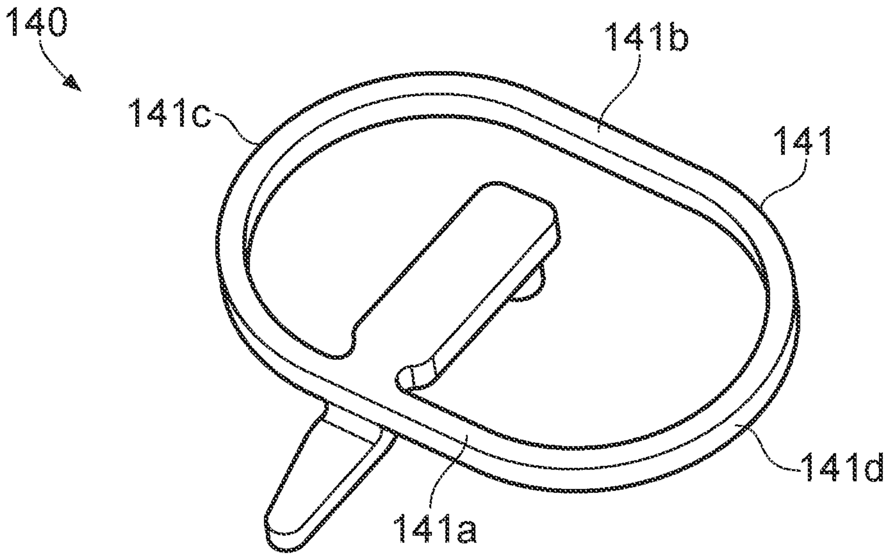
FIG. 3A is a perspective view of a first side of a locking component according to an embodiment.

FIG. 3A illustrates a first side of the locking component 140 according to an embodiment. The locking component 140 comprises a compliant body 141. The compliant body 141 is planar, that is to say, it lies in a plane. The compliant body 141 is stadium-shaped, that is to say, the compliant body is formed in the shape of a stadium, otherwise known as a discorectangle or an obround. The compliant body 141 may be defined by a rectangle with semicircles at a pair of opposite side. The compliant body 141 may have a plane shape consisting of two semicircles connected by parallel lines tangent to their endpoints.

In the arrangement shown, the compliant body 141 comprises a first straight portion 141*a* and a second straight portion 141*b*. The first and second straight portions 141*a*, 141*b* have the same length and are positioned parallel to one another. The compliant body 141 further comprises a first semi-circular portion 141*c* and a second semi-circular portion 141*d*. A first end of each of the semi-circular portions 141*c*, 141*d* is connected to the first straight portion 141*a* and a second end of each of the semi-circular portions 141*c*, 141*d* is connected to the second straight portion 141*b*. The perpendicular separation between the straight portions 141*a*, 141*b* is equal to the diameter of each semi-circular portion 141*c*, 141*d*. The compliant body 141 may have an axis of symmetry lying midway between the straight portions 141*a*, 141*b* and extending parallel thereto. The compliant body 141 may have an axis of symmetry bisecting the straight portions 141*a*, 141*b*.

As shown, the compliant body 141 is a closed loop. The material that defines the loop has a quadrilateral cross section. In some arrangements, the cross section may be a rectangle or a square. In the arrangement shown, one of the pairs of opposite surfaces of the rectangular cross section is parallel to the plane in which the compliant body 141 is defined. The shape of the compliant body 141 is configured to act as a biasing means. In this way, the compliant body 141 will deform when a force is applied thereto and, once the force is removed, it will return to its equilibrium or resting position as shown in FIG. 3A. The compliant body 141 is particularly flexible when deformed in a direction that lies in the plane of the compliant body 141 and that is substantially perpendicular to the straight portions 141*a*, 141*b*. The compliant body 141 is preferably not a coil spring.

Figure 3B:
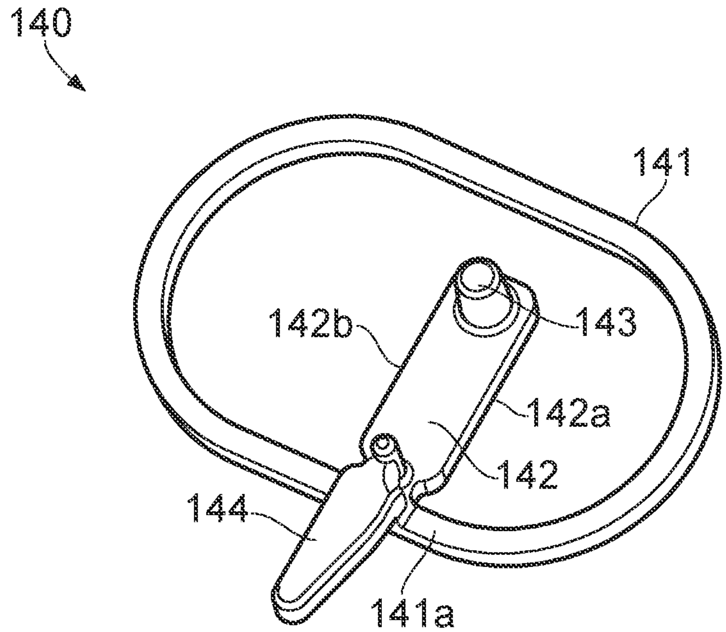
FIG. 3B is a perspective view of a second side of the locking component according to an embodiment.

FIG. 3B illustrates a second side of the locking component 140. The locking component 140 comprises a latch member 143. In the arrangement shown, the first latch member 143 is a cylinder extending from the plane of the compliant body 141 in a direction perpendicular to the plane of the compliant body 141. As will be described later, the first latch member 143 is configured to prevent the blade from being deployed when the jaw members are in the open position. This can be achieved by the first latch member 143 comprising a pin, configured to be received in a slot or notch comprised in the blade. In alternative arrangements, the locking mechanism may be configured in an opposite manner, such that the latch member of the locking component 140 may be a slot or notch configured to receive a pin fixed to the blade. Therefore, the locking component 140 comprises a latch member configured to mechanically interact with the blade. In this way, such a mechanical interaction may be achieved by any suitably cooperating components on the locking component and the blade such that the locking component is configured to be releasably connected to the blade.

The first latch member 143 is connected to and located within the compliant body 141. That is to say, the first latch member 143 is positioned on the locking component 140 within the boundary defined by the compliant body 141. With respect to the plane of the compliant body 140, at least a portion of the first latch member 143 is comprised within the closed loop of the compliant body 141. In the example shown, the latch member 143 is positioned between the straight portions 141*a*, 141*b* and between the semi-circular portions 141*c*, 141*d* of the compliant body 141.

The locking component 140 comprises a rib 142 fixed to the compliant body 141. The rib 142 is fixed at a single point along the compliant body 141. In the arrangement shown, the rib 142 extends from the first straight portion 141*a* of the compliant body 141 in the plane thereof, towards the second straight portion 141*b*. In this way, the rib 142 extends into the boundary of the compliant body 141, that is to say, into the interior of the closed loop. In the arrangement shown, the rib 142 is fixed to only one of the portions 141*a*, 141*b*, 141*c*, 141*d* of the compliant body 141.

The rib 142 is substantially planar. In the arrangement shown in FIG. 3B, the rib is substantially rectangular and comprises a first side 142*a* and a second side 142*b*, opposite and parallel to the first side 142*a*. The rib 142 is arranged such that the two straight sides 142*a*, 142*b* are perpendicular to the straight portions 141*a*, 141*b* of the compliant body 141. As will be described later, the sides 142*a*, 142*b* are configured to slide along a part of the handle portion 121 in order to constrain the movement of the rib 142. The first latch member 143 is connected to the compliant body 141 by the rib 142. A proximal end of the rib 142 is fixed to the compliant body 141 while the first latch member 143 is comprised at a distal end of the rib 142. In the arrangement shown, in which the latch member 143 is a pin, the pin extends from the rib 142 in a direction perpendicular to the plane thereof.

The locking component may further comprise an arm 144. The arm 144 is a protrusion extending from the compliant body 141. The arm 144 may extend from the same portion of the compliant body 141 as the rib 142. In the arrangement shown, the arm 144 extends from the first straight portion 141*a* of the compliant body 141. The arm 144 may extend from substantially the same point along the compliant body 141 as the rib 142. The arm 144 extends outwardly from the compliant body 141 in a direction substantially parallel to the plane thereof. Therefore, the arm 144 may extend from the compliant body 141 in an opposite direction to the rib 142. In the arrangement shown, the arm 144 is fixed to the first straight portion 141*a* and extends in a direction away from the second straight portion 141*b* of the compliant body 141. In this way, the arm 144 lies outside of the boundary of the compliant body 141, that is to say, outside of the loop.

Any or all parts of the locking component may comprise a polymer and may be formed by injection moulding or additive manufacturing, such as 3D printing. The locking component may consist solely of a polymer material. The locking component 140 may consist solely of the compliant body and the latch member. The locking component 140 may consist solely of the compliant body 141, the rib 142 and the latch member 143. The locking component 140 may consist solely of the compliant body 141, the rib 142, the latch member 143 and the arm 144. The locking component 140 may comprise a single integral component. That is to say, the parts of the locking component 140 may be formed integrally with the locking component 140 without the need to fix or connect separate pieces together. Preferably, the locking component is formed of a single moulding and is more preferably formed of a single polymer moulding, which may be manufactured using injection moulding.

Figure 4:
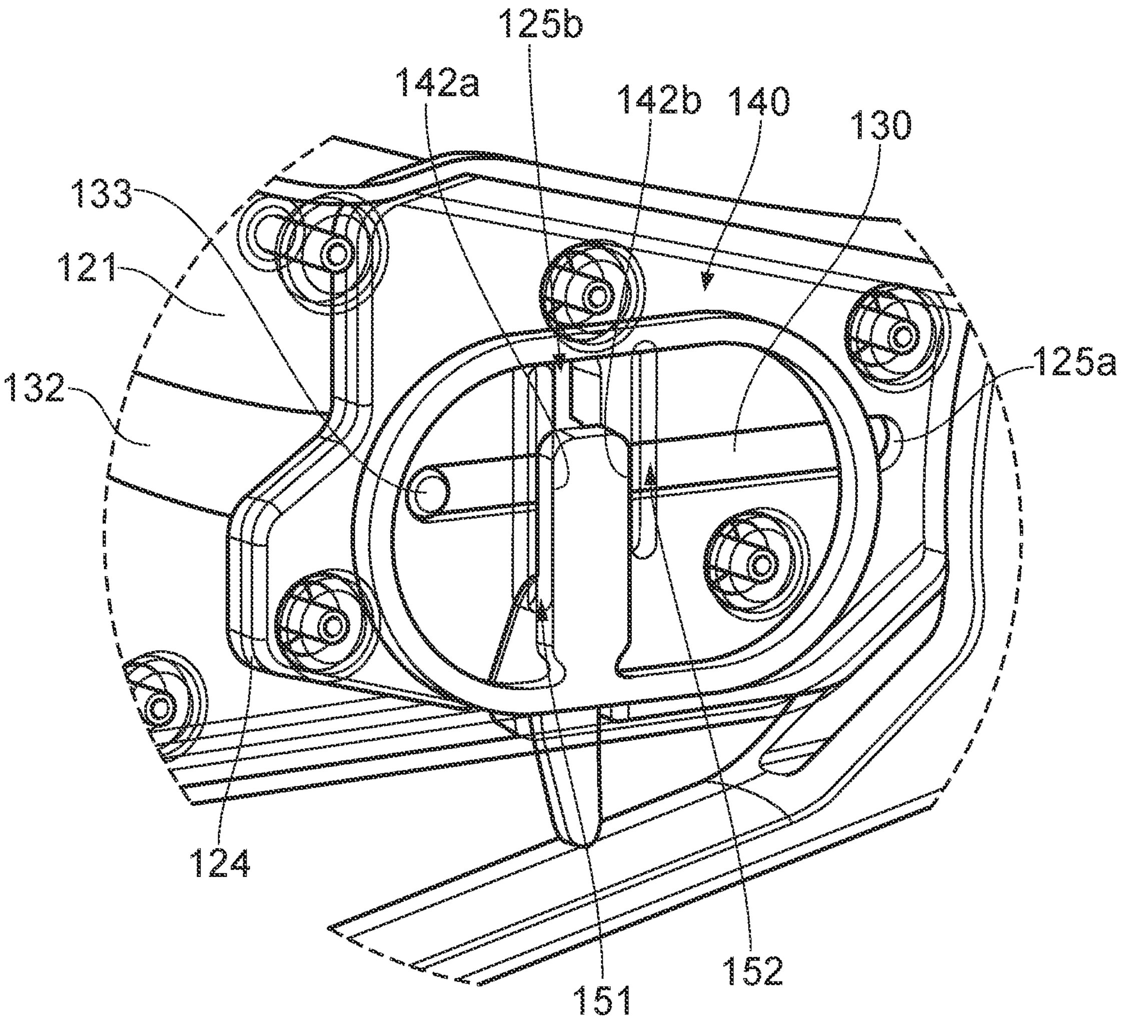
FIG. 4 is a perspective view of a first side of part of a surgical device having a locking component according to an embodiment.

FIG. 4 illustrates part of the surgical device 100 as viewed from a first side. In particular, FIG. 4 shows the internal details of the handle portion 121 of the hand-piece 120 and demonstrates how the locking component 140, described above, can be comprised in the surgical device 100. The handle portion 121 comprises first and second sidewalls that can be fixed together by any suitable fastening means. In the arrangement shown, the sidewalls are fixed together by a clamshell assembly in which the sidewalls can be press-fitted together by the communication between one or more pins and one or more holes. The handle portion 121 further comprises a support 124. The support is comprised within the handle portion 121 between the sidewalls. The support 124 is substantially planar and lies in a plane substantially parallel to the plane of at least one of the sidewalls. The support 124 may comprise one or more holes to accommodate the fastening means connecting the sidewalls together. In this way, the support 124 is fixed relative to the handle portion 121. The support 124 further comprises a blade track 125*a*. The blade track 125*a* is an aperture through the support 124 that extends parallel to the longitudinal axis of the surgical device 100 and/or the blade 130.

At least a portion of the blade 130 is comprised in the handle portion 121. In FIG. 4, the blade 130 is positioned behind the support 124. FIG. 4 also shows a trigger arm 132 which forms part of the trigger mechanism operable to deploy the blade 130. The blade 130 is pivotally connected to the trigger arm 132 by a pivot pin 133. The pivot pin 133 can be received by the blade track 125*a* and is configured to slide along the blade track 125*a* when the blade 130 moves axially with respect to the support 124.

The first side of the locking component 140 can also be seen in FIG. 4. The locking component 140 is shown here in its first position. The locking component 140 is held in the handle portion 121, preferably sandwiched between the first sidewall and the support 124. In the arrangement shown, the plane of the compliant body 141 is parallel to the plane of the support 124. The second side of the locking component 140, that is the side on which the first latch member 143 is comprised, may face the support 124 while the first side of the locking component 140 may face the first sidewall of the handle portion 121.

The first sidewall of the handle portion 121 comprises one or more rails. In the arrangement shown, the handle portion 121 comprises a first rail 151 and a second rail 152. The rails 151, 152 are straight ridges on an internal surface of the handle portion 121 and are parallel to one another. The rails 151, 152 may extend in a direction perpendicular to the longitudinal axis of the surgical device and/or to the longitudinal axis of the blade 130. The rails 151, 152 are spaced so as to receive the rib 142. In the arrangement shown, the first side 142*a* of the rib 142 is configured to slide along the first rail 151 while the second side 142*b* of the rib 142 is configured to slide along the second rail 152. In this way, the rails 151, 152 are configured as a guide for the rib 142 to constrain the movement of the rib 142 in a direction perpendicular to the blade 130.

Although it is not visible in FIG. 4, the first latch member 143 projects from the rib 142 towards the second sidewall. To accommodate this, a notch 125*b* is provided in the support 124. The notch 125*b* is configured to allow the first latch member 143 to slide therealong in a direction perpendicular to the longitudinal axis and parallel to the rails 151, 152. In the arrangement shown, the notch 125*b* is an aperture through the thickness of the support 124 and is a transverse extension of the blade track 125*a*. Therefore, the blade track 125*a* and the notch 125*b* form a T-shaped aperture in the support 124 to allow the pivot pin 133 to slide axially and to allow the first latch member 143 to slide transversely, with respect to the support 124.

Figure 5:
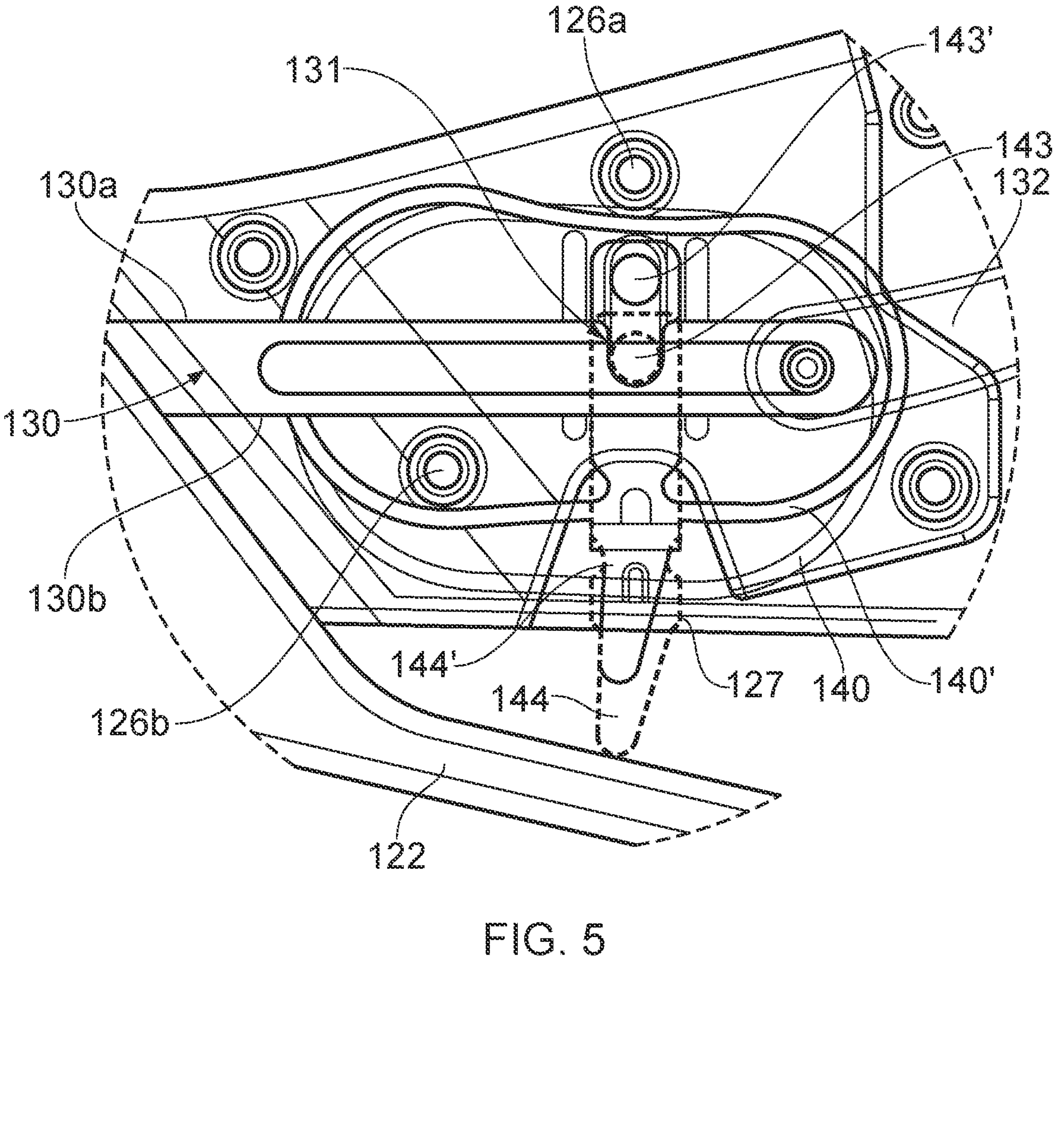
FIG. 5 is a side view of a second side of part of a surgical device having a locking component according to an embodiment.

FIG. 5 illustrates part of the surgical device 100 as viewed from a second side, that is, the opposite side to the view in FIG. 4. The first position of the locking component 140 and parts thereof is shown in phantom lines and labelled using the same reference numerals as in FIGS. 2 to 4, while the second position of the locking component 140' and parts thereof is labelled using the corresponding reference numerals with a prime (') symbol.

Additional details of the blade 130 are illustrated in FIG. 5. The blade comprises a first edge 130*a* and a second edge 130*b*. The blade 130 is positioned in the handle portion 121 such that the edges 130*a*, 130*b* lie in the same plane that is parallel to the plane of the support 124. Furthermore, the blade 130 is arranged such that the second edge 130*b* is disposed between the first edge 130*a* and the lever 122.

The blade 130 comprises a second latch member 131 configured to mechanically interact with the first latch member 143 on the locking component 140. In the arrangement shown, the second latch member 131 is a cut-out portion through the thickness of the blade 130. The second latch member 131 is comprised in the first edge 130*a* of the blade 130. In this way, the second latch member 131 faces away from the lever 122. The second latch member 131 is sized and shaped so as to cooperate with the first latch member 143. In the illustrated arrangement, the first latch member is a pin 143 and the second latch member is a slot 131 configured to receive the pin 143. The second latch member 131 is configured to allow the first latch member 143 to move in and out thereof. It will be appreciated that other cooperating components able to facilitate a mechanical interaction between the locking component 140 and the blade 130 could be employed instead of, or in addition to, a pin in a corresponding slot.

In a first position, the first latch member 143 is engaged with the second latch member 131 such that the blade 130 is prevented from moving along its axis. Therefore, the latch member 143 of the locking component 140 prevents deployment of the blade 130 when in a first position. In a second position, the first latch member 143' is disengaged from the second latch member 131 such that the blade 130 can move along its axis. Therefore, the latch member 143' of the locking component 140' does not hinder the motion of the blade 130, and therefore allows the trigger mechanism to deploy the blade 130.

As shown in FIGS. 4 and 5, the support 124 is positioned between the blade 130 and the locking component 140. The first latch member 143 extends through the notch 125*b* of the support 124 in order to engage the second latch member 131. The arm 144 of the locking component 140 extends out of the handle portion 122 via an aperture 127 provided therein in order to contact the lever 122. In this way, the locking component 140 is configured to move in response to manipulation of the lever 122. The locking component 140 is positioned in the handle portion 121 such that the first straight portion 141*a* of the compliant body 141, i.e. the portion to which the latch member is connected, is closer to the lever 122 than the second straight portion 141*b*. In other words, the first straight portion 141*a* is positioned between the lever 122 and the second straight portion 141*b*.

As mentioned above, the sidewalls of the handle portion 121 are fixed together by any suitable fastening means. In the arrangement shown, at least one of the fastening means is configured to limit the movement of the locking component 140. In particular, a first limiter 126*a* and a second limiter 126*b* extend from the first sidewall to the second sidewall of the handle portion 121, through holes in the support 124. The first limiter 126*a* is positioned in proximity to the second straight portion 141*b* and outside of the boundary of the compliant body 141. In particular, the first limiter 126*a* is positioned along the axis of motion of the rib 142 and the latch member 143. Otherwise stated, the first limiter 126*a* is located along a transverse axis defined by the rib 142, latch member 143 and notch 125*b*. The first limiter 126*a* may be substantially rounded so as to provide a smooth surface against which the compliant body 141 can bear. The second limiter 126*b* may be positioned in proximity to the first straight portion 141*a* and inside the boundary of the compliant body 141. The second limiter 126*b* may be located at a position offset from the transverse axis along which the rib 142 is able to slide. Preferably, the locking component 140 is not fixedly connected to any other component in the surgical device. Instead, the locking component 140 is free to move within the handle portion 121 subject to one or more mechanical constraints. As noted above, the rib 142 is constrained to slide along the rails 151, 152; the first latch member 143 is constrained to move along the notch 125*b*; and the compliant body 141 is constrained by one or more limiters (such as the first limiter 126*a*) in the handle portion 121.

The surgical device 100 is configured such that the handle 121 and lever 122 are held in an open position as shown in FIGS. 1 and 4. By virtue of the shape of the locking component 140 and its arrangement within the surgical device 100, the compliant body 141 acts as a biasing means to exert a reaction force against the first limiter 126*a* and thereby retain the first straight portion 141*a* towards the lever 122 and away from the second straight portion 141*b*. In this way, the compliant body 141 biases the rib 142 towards the lever 122 (i.e. downwards in FIGS. 4 and 5) such that the first latch member 143 engages the blade 130 via the second latch member 131, thereby preventing the blade 130 from being moved axially by the trigger arm 132.

In operation, a practitioner may position the first and second jaw members 111, 112 around tissue or one or more vessels and close the jaw members 111, 112 by forcing the handle 121 and the lever 122 towards each other. In doing so, the lever 122 forces the first latch member from its first position (143) to its second position (143'). In the arrangement shown, the lever 122 being forced towards the handle portion 121 moves the arm of the locking component from a first position (144) to a second position (144'). Given that the arm 144 is connected to the same portion of the compliant body 141 as the rib 142, this movement will force the rib 142 along the rails 151, 152 towards the first limiter 126*a* (i.e. upwards in FIGS. 4 and 5). Accordingly, the first latch member 143 is also moved towards the limiter 126*a* and is released from the second latch member 131. While holding the lever 122 closed such that the first latch member is in its second position, the practitioner may operate the trigger mechanism to deploy the blade 130 such that it moves along its longitudinal axis towards the end effector 110 (i.e. to the left in FIG. 5) and protrudes out of a slot (not shown) provided between the first and second jaw members 111, 112, to thereby cut the required tissue. As mentioned above, the movement of the blade 130 may be constrained by the pivot pin 133 sliding along the blade track 125*a*.

Following this, the blade 130 may be automatically returned (i.e. to the right in FIG. 5) by the trigger mechanism to the position shown in FIG. 5, i.e. its resting position, such that the second latch member 131 is re-aligned with the first latch member 143 along the transverse axis. By reducing the force on the lever 122 to thereby allow it to be returned to its first position away from the handle portion 121, the compliant body 141 biases the first latch member from its second position (143') to its first position (143) in which it is engaged with the second latch member 131 by a mechanical interaction therewith.

Should a practitioner activate the trigger mechanism when the jaws 111, 112 are in the open position (i.e. when the lever 122 and the handle 121 are held away from one another), the mechanical interaction between the locking component 140 and the blade 130 will prevent the blade 130 from moving into its deployed position. Instead, the engagement between the first latch member 143 and the second latch member 131 may transfer the triggering force to the locking component 140. In view of the positioning of the first latch member 143 in the notch 125*b*, at least a portion of the triggering force may be transferred to the support 124 via the first latch member 143. Moreover, in view of the positioning of the rib 142 between the rails 151, 152, and in particular the second side 142*b* bearing against the second rail 152 (see FIG. 4), at least a portion of the triggering force may be transferred to the first sidewall via the rib 142.

Various modifications, whether by way of addition, deletion and/or substitution, may be made to all of the above described embodiments to provide further embodiments, any and/or all of which are intended to be encompassed by the appended claims.

The invention claimed is:

1. A locking component for a surgical device configured to prevent deployment of a blade when a first jaw member and a second jaw member of the surgical device are disposed in an open position and to permit deployment of the blade when the first and second jaw members are disposed in a closed position, the locking component comprising:

a latch member, configured to engage the blade to prevent deployment of the blade by a mechanical interaction therewith when the latch member is in a first position; and a compliant body, connected to and disposed around the latch member, wherein the compliant body is configured to:

when a force is applied to the compliant body, deform and move the latch member out of the first position into a second position in which the latch member is disengaged from the blade, thereby allowing deployment of the blade; and when the force is removed, bias the latch member to return to the first position such that the latch member engages the blade, thereby preventing deployment of the blade.

2. The locking component according to claim 1, wherein the compliant body is a closed loop.

3. The locking component according to claim 1, wherein the compliant body is parallel to a first plane and is configured to exert a biasing force in a direction parallel to the first plane.

4. The locking component according to claim 3, wherein the latch member comprises a protrusion from the locking component in a direction perpendicular to the first plane.

5. The locking component according to claim 3, further comprising a rib, configured to be slideably received by the surgical device so as to constrain movement of the latch member in the first plane.

6. The locking component according to claim 5, wherein the latch member and the compliant body are connected by the rib.

7. The locking component according to claim 5, wherein the latch member comprises a protrusion from the rib.

8. The locking component according to claim 1, wherein the latch member and the compliant body comprise an integral component.

9. The locking component according to claim 1, wherein the latch member and the compliant body comprise a single moulding.

10. The locking component according to claim 1, wherein a cross section of at least a portion of the compliant body is rectangular.

11. The locking component according to claim 1, wherein the compliant body comprises first and second straight portions, the straight portions being joined together by first and second arc portions.

12. The locking component according to claim 11, wherein the first arc portion is configured to join together first ends of the first and second straight portions, and the second arc portion is configured to join together second ends of the first and second straight portions.

13. The locking component according to claim 11, wherein the first and second straight portions are parallel.

14. The locking component according to claim 1, wherein the compliant body is stadium-shaped.

15. The locking component according to claim 1, further comprising an arm, provided in fixed relation to the latch member and configured to transfer a force to the latch member to thereby move it away from the first position.

16. The locking component according to claim 15, wherein the latch member, the compliant body and the arm are comprised in a single integral component.

17. A surgical device comprising:

a hand piece;

first and second jaw members extending from the hand piece, configured to be opened and closed in response to manipulation of the hand piece;

a locking component including a first latch member and compliant body; and a blade assembly including:

a blade comprising a second latch member; and a trigger mechanism for deploying the blade towards the first and second jaw members, wherein:

the first latch member of the locking component is configured to engage with the second latch member of the blade when the first latch member is in a first position, in order to prevent deployment of the blade, and wherein the compliant body is configured to:

when the first and second jaw members are closed, deform and move the first latch member out of the first position into a second position in which the first latch member is disengaged from the second latch member, thereby allowing deployment of the blade using the trigger mechanism; and when the first and second jaw members are opened, bias the first latch member to return to the first position such that the first latch member engages the second latch member, thereby preventing deployment of the blade.

18. The surgical device according to claim 17, wherein the first latch member and the compliant body are comprised in a single moulded component.

19. The surgical device according to claim 17, wherein the first and second jaw members are provided with respective opposing electrically conductive plates on inner opposing surfaces thereof, the electrically conductive plates being connectable in use via respective connections to an RF electrosurgical generator so as to receive, in use, an RF electrosurgical signal.

20. A method of operating a surgical device having a hand-piece, opposing jaw members extending from the hand-piece, a blade and a locking component, the locking component comprising a compliant body and a latch member configured to engage the blade to prevent deployment of the blade when the latch member is in a first position, the method comprising:

manipulating the hand-piece to close the opposing jaw members, wherein closing the jaw members exerts a force on the compliant body such that the compliant body deforms and moves the latch member away from the first position into a second position so as to disengage from the blade;

activating a trigger mechanism to deploy the blade; and manipulating the hand-piece to open the opposing jaw members, wherein opening the jaw members removes the force on the compliant body and the compliant body biases the latch member to return to the first position such that the latch member engages the blade and prevents deployment of the blade.

* * * * *